United States Patent
Omarsson et al.

(10) Patent No.: US 10,512,305 B2
(45) Date of Patent: Dec. 24, 2019

(54) TIGHTENING SYSTEM WITH A TENSION CONTROL MECHANISM

(71) Applicant: OSSUR HF, Reykjavik (IS)

(72) Inventors: Bjorn Omarsson, Reykjavik (IS); Harry Duane Romo, Aliso Viejo, CA (US); Janaki Ram-srinivasaRao Chetlapalli, Irvine, CA (US)

(73) Assignee: OSSUR HF, Reykjavik (IS)

( * ) Notice: Subject to any disclaimer, the term of this patent is extended or adjusted under 35 U.S.C. 154(b) by 1162 days.

(21) Appl. No.: 14/794,945

(22) Filed: Jul. 9, 2015

(65) Prior Publication Data

US 2016/0009523 A1    Jan. 14, 2016

Related U.S. Application Data

(60) Provisional application No. 62/023,673, filed on Jul. 11, 2014.

(51) Int. Cl.
*A43C 11/16* (2006.01)
*B65H 75/44* (2006.01)
*A61F 5/01* (2006.01)

(52) U.S. Cl.
CPC .............. *A43C 11/165* (2013.01); *A61F 5/01* (2013.01); *B65H 75/4428* (2013.01); *B65H 75/4492* (2013.01); *B65H 2701/35* (2013.01); *B65H 2701/537* (2013.01); *B65H 2701/71* (2013.01)

(58) Field of Classification Search
CPC ............ B65H 75/4428; B65H 75/4492; B65H 2701/71; B65H 2701/35; B65H 2701/537; A43C 11/165
See application file for complete search history.

(56) References Cited

U.S. PATENT DOCUMENTS

| | | |
|---|---|---|
| 73,768 A | 1/1868 | Allen |
| 1,601,659 A | 9/1926 | Van Harlingen |
| 2,070,093 A | 2/1937 | Roe |
| 2,195,024 A | 3/1940 | Bullock |
| 2,467,907 A | 4/1949 | Peckham |
| 2,536,454 A | 1/1951 | McIntyre |
| 2,558,986 A | 7/1951 | Seelert |
| 2,959,168 A | 11/1960 | Shook |

(Continued)

FOREIGN PATENT DOCUMENTS

| | | |
|---|---|---|
| CA | 2 112 789 A1 | 8/1994 |
| CA | 2 114 387 A1 | 8/1994 |

(Continued)

OTHER PUBLICATIONS

"Rollerblade TFS Skate Laces AERO", http://www.inlinewarehouse.com/viewlarge.html?PCODE=TFS, retrieved on Jan. 7, 2010, 1 page.

(Continued)

*Primary Examiner* — Abigail E Troy
(74) *Attorney, Agent, or Firm* — Workman Nydegger

(57) ABSTRACT

A tightening system includes a housing and a spool situated within the housing. The spool is rotatable about an axis within the housing. An elongate tensioning element is rotatably linked to the spool and a tension control mechanism is operatively connected to the spool. The tension control mechanism is arranged to automatically move relative to the spool when tension in the tensioning element reaches a predetermined level, which, in turn, releases at least part of the tension in the tensioning element.

14 Claims, 4 Drawing Sheets

(56) References Cited

U.S. PATENT DOCUMENTS

| | | |
|---|---|---|
| 3,311,319 A | 3/1967 | Campbell |
| 3,444,560 A | 5/1969 | Northup, Jr. |
| 3,516,382 A | 6/1970 | Ferraro |
| 3,753,625 A | 8/1973 | Fabrizio et al. |
| 3,793,749 A | 2/1974 | Gertsch et al. |
| 3,808,644 A | 5/1974 | Schoch |
| 3,889,664 A | 6/1975 | Heuser et al. |
| 3,926,182 A | 12/1975 | Stabholz |
| 3,976,057 A | 8/1976 | Barclay |
| 4,064,569 A | 12/1977 | Campbell |
| 4,088,130 A | 5/1978 | Applegate |
| 4,100,918 A | 7/1978 | Glancy |
| 4,145,766 A | 3/1979 | May |
| 4,220,148 A | 9/1980 | Lehneis |
| 4,261,081 A | 4/1981 | Lott |
| 4,298,992 A | 11/1981 | Burnstein et al. |
| 4,320,747 A | 3/1982 | Daniell, Jr. |
| 4,340,041 A | 7/1982 | Frank |
| 4,361,142 A | 11/1982 | Lewis et al. |
| 4,370,977 A | 2/1983 | Mauldin et al. |
| 4,372,298 A | 2/1983 | Lerman |
| 4,407,276 A | 10/1983 | Bledsoe |
| 4,428,369 A | 1/1984 | Peckham et al. |
| 4,433,456 A | 2/1984 | Baggio |
| 4,433,679 A | 2/1984 | Mauldin et al. |
| 4,463,751 A | 8/1984 | Bledsoe |
| 4,506,661 A | 3/1985 | Foster |
| 4,520,802 A | 6/1985 | Mercer et al. |
| 4,523,585 A | 6/1985 | Lamb et al. |
| 4,551,932 A | 11/1985 | Schoch |
| 4,555,830 A | 12/1985 | Petrini et al. |
| 4,574,500 A | 3/1986 | Aldinio et al. |
| 4,616,524 A | 10/1986 | Bidoia |
| 4,619,657 A | 10/1986 | Keates et al. |
| 4,620,378 A | 11/1986 | Sartor |
| 4,631,839 A | 12/1986 | Bonetti et al. |
| 4,631,840 A | 12/1986 | Gamm |
| 4,633,599 A | 1/1987 | Morell et al. |
| 4,649,906 A | 3/1987 | Spademan |
| 4,654,985 A | 4/1987 | Chalmers |
| 4,655,201 A | 4/1987 | Pirmantgen |
| 4,660,300 A | 4/1987 | Morell et al. |
| 4,660,302 A | 4/1987 | Arieh et al. |
| 4,680,878 A | 7/1987 | Pozzobon et al. |
| 4,691,694 A | 9/1987 | Boyd et al. |
| 4,697,583 A | 10/1987 | Mason et al. |
| 4,719,670 A | 1/1988 | Kurt |
| 4,719,709 A | 1/1988 | Vaccari |
| 4,719,710 A | 1/1988 | Pozzobon |
| 4,723,539 A | 2/1988 | Townsend |
| 4,732,143 A | 3/1988 | Kausek et al. |
| 4,733,656 A | 3/1988 | Marquette |
| 4,741,115 A | 5/1988 | Pozzobon |
| 4,748,726 A | 6/1988 | Schoch |
| 4,760,653 A | 8/1988 | Baggio |
| 4,768,762 A | 9/1988 | Lund |
| 4,773,404 A | 9/1988 | Townsend |
| 4,790,299 A | 12/1988 | Marquette |
| 4,793,333 A | 12/1988 | Marquette |
| 4,799,297 A | 1/1989 | Baggio et al. |
| 4,802,291 A | 2/1989 | Sartor |
| 4,811,503 A | 3/1989 | Iwama |
| 4,817,588 A | 4/1989 | Bledsoe |
| 4,841,649 A | 6/1989 | Baggio et al. |
| 4,856,500 A | 8/1989 | Spademan |
| 4,856,501 A | 8/1989 | Castillo et al. |
| 4,865,024 A | 9/1989 | Hensley et al. |
| 4,884,760 A | 12/1989 | Baggio et al. |
| 4,890,607 A | 1/1990 | Townsend |
| 4,911,709 A | 3/1990 | Marlow et al. |
| 4,955,369 A | 9/1990 | Bledsoe et al. |
| 4,961,416 A | 10/1990 | Moore et al. |
| 4,961,544 A | 10/1990 | Bidoia |
| 4,966,133 A | 10/1990 | Kausek |
| 4,982,732 A | 1/1991 | Morris |
| 4,991,571 A | 2/1991 | Kausek |
| 5,002,045 A | 3/1991 | Spademan |
| 5,018,514 A | 5/1991 | Grood et al. |
| 5,020,797 A | 6/1991 | Burns |
| 5,038,765 A | 8/1991 | Young et al. |
| 5,042,177 A | 8/1991 | Schoch |
| 5,052,375 A | 10/1991 | Stark et al. |
| 5,062,225 A | 11/1991 | Gorza |
| 5,063,917 A | 11/1991 | Young et al. |
| 5,065,481 A | 11/1991 | Walkhoff |
| 5,092,321 A | 3/1992 | Spademan |
| 5,117,567 A | 6/1992 | Berger |
| 5,152,038 A | 10/1992 | Schoch |
| 5,157,813 A | 10/1992 | Carroll |
| 5,176,622 A | 1/1993 | Anderson et al. |
| 5,177,882 A | 1/1993 | Berger |
| 5,181,331 A | 1/1993 | Berger |
| 5,183,036 A | 2/1993 | Spademan |
| 5,213,094 A | 5/1993 | Bonutti |
| 5,230,696 A | 7/1993 | Silver et al. |
| 5,230,697 A | 7/1993 | Castillo et al. |
| 5,249,377 A | 10/1993 | Walkhoff |
| 5,261,871 A | 11/1993 | Greenfield |
| 5,319,868 A | 6/1994 | Hallenbeck |
| 5,325,613 A | 7/1994 | Sussmann |
| 5,327,662 A | 7/1994 | Hallenbeck |
| 5,347,894 A | 9/1994 | Fischer |
| 5,357,654 A | 10/1994 | Hsing-Chi |
| 5,365,947 A | 11/1994 | Bonutti |
| 5,388,877 A | 2/1995 | Wenk |
| 5,433,648 A | 7/1995 | Frydman |
| 5,437,611 A | 8/1995 | Stern |
| 5,437,619 A | 8/1995 | Malewicz et al. |
| 5,443,444 A | 8/1995 | Pruyssers |
| 5,456,268 A | 10/1995 | Bonutti |
| 5,472,410 A | 12/1995 | Hamersly |
| 5,472,412 A | 12/1995 | Knoth |
| 5,477,593 A | 12/1995 | Leick |
| 5,502,902 A | 4/1996 | Sussmann |
| 5,514,082 A | 5/1996 | Smith, III |
| 5,588,956 A | 12/1996 | Billotti |
| 5,599,288 A | 2/1997 | Shirley et al. |
| 5,628,722 A | 5/1997 | Solomonow et al. |
| 5,638,588 A | 6/1997 | Jungkind |
| 5,647,104 A | 7/1997 | James |
| 5,658,241 A | 8/1997 | Deharde et al. |
| 5,662,596 A | 9/1997 | Young |
| 5,669,116 A | 9/1997 | Jungkind |
| 5,685,830 A | 11/1997 | Bonutti |
| 5,732,483 A | 3/1998 | Cagliari |
| 5,737,854 A | 4/1998 | Sussmann |
| 5,807,294 A | 9/1998 | Cawley et al. |
| 5,819,378 A | 10/1998 | Doyle |
| 5,827,208 A | 10/1998 | Mason et al. |
| 5,848,979 A | 12/1998 | Bonutti et al. |
| 5,857,988 A | 1/1999 | Shirley |
| 5,873,847 A | 2/1999 | Bennett et al. |
| 5,891,061 A | 4/1999 | Kaiser |
| 5,891,071 A | 4/1999 | Sterns et al. |
| 5,921,946 A | 7/1999 | Tillinghast et al. |
| 5,934,599 A | 8/1999 | Hammerslag |
| 5,950,245 A | 9/1999 | Binduga |
| 5,954,677 A | 9/1999 | Albrecht et al. |
| 5,997,493 A | 12/1999 | Young |
| 6,004,283 A | 12/1999 | Young |
| 6,074,355 A | 6/2000 | Bartlett |
| 6,110,137 A | 8/2000 | Bastyr et al. |
| 6,129,690 A | 10/2000 | Hamlin et al. |
| 6,159,248 A | 12/2000 | Gramnas |
| 6,202,953 B1 | 3/2001 | Hammerslag |
| 6,206,932 B1 | 3/2001 | Johnson |
| RE37,209 E | 6/2001 | Hensley et al. |
| RE37,297 E | 7/2001 | Smith, III |
| 6,256,798 B1 | 7/2001 | Egolf et al. |
| 6,267,390 B1 | 7/2001 | Maravetz et al. |
| 6,289,558 B1 | 9/2001 | Hammerslag |
| 6,290,664 B1 | 9/2001 | Nauert |
| 6,331,169 B1 | 12/2001 | Bastyr et al. |
| 6,409,693 B1 | 6/2002 | Brannigan |

(56) References Cited

U.S. PATENT DOCUMENTS

| | | |
|---|---|---|
| 6,413,232 B1 | 7/2002 | Townsend et al. |
| 6,416,074 B1 | 7/2002 | Maravetz et al. |
| 6,425,166 B1 | 7/2002 | Seligman et al. |
| 6,502,577 B1 | 1/2003 | Bonutti |
| 6,503,213 B2 | 1/2003 | Bonutti |
| 6,551,264 B1 | 4/2003 | Cawley et al. |
| 6,666,837 B2 | 12/2003 | Weihermuller |
| 6,689,080 B2 | 2/2004 | Castillo |
| 6,711,787 B2 | 3/2004 | Jungkind et al. |
| 6,740,054 B2 | 5/2004 | Sterns |
| 6,752,775 B2 | 6/2004 | Seligman et al. |
| 6,769,155 B2 | 8/2004 | Hess et al. |
| 6,770,047 B2 | 8/2004 | Bonutti |
| 6,827,653 B2 | 12/2004 | Be |
| 6,875,187 B2 | 4/2005 | Castillo |
| 6,921,377 B2 | 7/2005 | Bonutti |
| 6,936,020 B2 | 8/2005 | Davis |
| 6,993,808 B1 | 2/2006 | Bennett et al. |
| 7,004,919 B2 | 2/2006 | Gaylord et al. |
| D519,637 S | 4/2006 | Nordt et al. |
| D520,141 S | 5/2006 | Nordt et al. |
| D521,644 S | 5/2006 | Nordt et al. |
| 7,037,287 B2 | 5/2006 | Cormier et al. |
| 7,059,329 B2 | 6/2006 | Mason et al. |
| 7,074,201 B2 | 7/2006 | Reinecke et al. |
| 7,097,627 B2 | 8/2006 | Enzerink et al. |
| 7,117,569 B2 | 10/2006 | Bledsoe |
| 7,128,724 B2 | 10/2006 | Marsh |
| 7,134,224 B2 | 11/2006 | Elkington et al. |
| 7,150,721 B2 | 12/2006 | Houser |
| 7,182,740 B1 | 2/2007 | Castillo |
| 7,192,407 B2 | 3/2007 | Seligman et al. |
| 7,198,610 B2 | 4/2007 | Ingimundarson et al. |
| 7,201,728 B2 | 4/2007 | Sterling |
| 7,207,126 B2 | 4/2007 | Gantier |
| 7,207,960 B2 | 4/2007 | Kenney |
| 7,235,058 B2 | 6/2007 | Doty et al. |
| 7,235,059 B2 | 6/2007 | Mason et al. |
| 7,281,341 B2 | 10/2007 | Reagan et al. |
| 7,306,573 B2 | 12/2007 | Bonutti |
| 7,309,322 B2 | 12/2007 | Albrecht et al. |
| 7,311,687 B2 | 12/2007 | Hoffmeier et al. |
| 7,331,126 B2 | 2/2008 | Johnson |
| 7,374,125 B2 | 5/2008 | Lin |
| 7,402,147 B1 | 7/2008 | Allen |
| 7,404,804 B2 | 7/2008 | Bonutti |
| 7,416,565 B1 | 8/2008 | Al-Turaikl |
| 7,431,708 B2 | 10/2008 | Sreeramagiri |
| 7,435,234 B2 | 10/2008 | Gamada |
| 7,438,698 B2 | 10/2008 | Daiju |
| 7,485,103 B2 | 2/2009 | Mason et al. |
| 7,500,957 B2 | 3/2009 | Bledsoe |
| 7,513,018 B2 | 4/2009 | Koenig et al. |
| 7,534,217 B2 | 5/2009 | Seligman et al. |
| 7,534,219 B2 | 5/2009 | Sterns |
| 7,544,174 B2 | 6/2009 | Nathanson |
| 7,553,289 B2 | 6/2009 | Cadichon |
| 7,591,050 B2 | 9/2009 | Hammerslag |
| 7,597,675 B2 | 10/2009 | Ingimundarson et al. |
| 7,600,660 B2 | 10/2009 | Kasper et al. |
| 7,617,573 B2 | 11/2009 | Chen |
| 7,618,386 B2 | 11/2009 | Nordt, III et al. |
| 7,618,389 B2 | 11/2009 | Nordt, III et al. |
| 7,662,122 B2 | 2/2010 | Sterling |
| 7,670,306 B2 | 3/2010 | Nordt, III et al. |
| 7,699,797 B2 | 4/2010 | Nordt, III et al. |
| 7,704,219 B2 | 4/2010 | Nordt, III et al. |
| 7,722,555 B2 | 5/2010 | Doty et al. |
| 7,757,303 B2 | 7/2010 | Miller |
| 7,806,842 B2 | 10/2010 | Stevenson et al. |
| 7,811,242 B2 | 10/2010 | Seligman |
| 7,846,115 B2 | 12/2010 | Seligman et al. |
| 7,850,632 B2 | 12/2010 | Gilmour |
| 7,857,776 B2 | 12/2010 | Frisbie |
| 7,862,621 B2 | 1/2011 | Kloos et al. |
| 7,874,955 B2 | 1/2011 | Patterson |
| 7,878,998 B2 | 2/2011 | Nordt, III et al. |
| 7,887,500 B2 | 2/2011 | Nordt, III et al. |
| 7,922,680 B2 | 4/2011 | Nordt, III et al. |
| 7,927,299 B2 | 4/2011 | Krause |
| 7,950,112 B2 | 5/2011 | Hammerslag et al. |
| 7,954,204 B2 | 6/2011 | Hammerslag et al. |
| 7,963,933 B2 | 6/2011 | Nace |
| 7,993,296 B2 | 8/2011 | Nordt, III et al. |
| 8,002,724 B2 | 8/2011 | Hu et al. |
| 8,038,635 B2 | 10/2011 | Dellanno |
| 8,038,637 B2 | 10/2011 | Bonutti |
| 8,048,013 B2 | 11/2011 | Ingimundarson et al. |
| 8,091,182 B2 | 1/2012 | Hammerslag et al. |
| 8,128,587 B2 | 3/2012 | Stevenson et al. |
| 8,920,350 B2 | 12/2014 | Merkley et al. |
| 2002/0013544 A1 | 1/2002 | Sterns |
| 2002/0052568 A1 | 5/2002 | Houser et al. |
| 2002/0095750 A1 | 7/2002 | Hammerslag |
| 2002/0133108 A1 | 9/2002 | Jagodzinski |
| 2002/0141755 A1 | 10/2002 | Manabe |
| 2003/0093882 A1 | 5/2003 | Gorza et al. |
| 2003/0204938 A1 | 11/2003 | Hammerslag |
| 2004/0002674 A1 | 1/2004 | Sterling |
| 2004/0049140 A1 | 3/2004 | Doty et al. |
| 2004/0054307 A1 | 3/2004 | Mason et al. |
| 2004/0054311 A1 | 3/2004 | Sterling |
| 2004/0068215 A1 | 4/2004 | Adelson et al. |
| 2004/0097859 A1 | 5/2004 | Sterns |
| 2005/0015156 A1 | 1/2005 | Hikichi |
| 2005/0020951 A1 | 1/2005 | Gaylord et al. |
| 2005/0081339 A1 | 4/2005 | Sakabayashi |
| 2005/0160627 A1 | 7/2005 | Dalgaard et al. |
| 2005/0177082 A1 | 8/2005 | Bledsoe |
| 2005/0245853 A1 | 11/2005 | Scorvo |
| 2005/0247813 A1 | 11/2005 | Kovacevich et al. |
| 2005/0273025 A1 | 12/2005 | Houser |
| 2005/0284003 A1 | 12/2005 | Dalgaard et al. |
| 2006/0015980 A1 | 1/2006 | Nordt, III et al. |
| 2006/0015988 A1 | 1/2006 | Philpott et al. |
| 2006/0020237 A1 | 1/2006 | Nordt, III et al. |
| 2006/0021204 A1 | 2/2006 | Young |
| 2006/0026733 A1 | 2/2006 | Nordt, III et al. |
| 2006/0026736 A1 | 2/2006 | Nordt, III et al. |
| 2006/0030802 A1 | 2/2006 | Nordt, III et al. |
| 2006/0030803 A1 | 2/2006 | Nordt, III et al. |
| 2006/0030804 A1 | 2/2006 | Nordt, III et al. |
| 2006/0030805 A1 | 2/2006 | Nordt, III et al. |
| 2006/0030806 A1 | 2/2006 | Nordt, III et al. |
| 2006/0070164 A1 | 4/2006 | Nordt, III et al. |
| 2006/0070165 A1 | 4/2006 | Nordt, III et al. |
| 2006/0100560 A1 | 5/2006 | Gilmour |
| 2006/0100561 A1 | 5/2006 | Gilmour |
| 2006/0116616 A1 | 6/2006 | Albrecht et al. |
| 2006/0135902 A1 | 6/2006 | Ingimundarson et al. |
| 2006/0142680 A1 | 6/2006 | Iarocci |
| 2006/0156517 A1 | 7/2006 | Hammerslag et al. |
| 2006/0174516 A1 | 8/2006 | Peruzzo |
| 2006/0185357 A1 | 8/2006 | Kovacevich et al. |
| 2006/0202077 A1 | 9/2006 | Kovacevich et al. |
| 2006/0202078 A1 | 9/2006 | Kovacevich et al. |
| 2007/0010772 A1 | 1/2007 | Ryan |
| 2007/0039085 A1 | 2/2007 | Kovacevich et al. |
| 2007/0100265 A1 | 5/2007 | Gamada |
| 2007/0169378 A1 | 7/2007 | Sodeberg et al. |
| 2007/0232972 A1 | 10/2007 | Martinez |
| 2007/0270976 A1 | 11/2007 | Deharde et al. |
| 2008/0034459 A1 | 2/2008 | Nordt, III et al. |
| 2008/0039757 A1 | 2/2008 | Nordt, III et al. |
| 2008/0039764 A1 | 2/2008 | Nordt, III et al. |
| 2008/0039765 A1 | 2/2008 | Nordt, III et al. |
| 2008/0039767 A1 | 2/2008 | Nordt, III et al. |
| 2008/0051684 A1 | 2/2008 | Gamada |
| 2008/0060167 A1 | 3/2008 | Hammerslag et al. |
| 2008/0060168 A1 | 3/2008 | Hammerslag et al. |
| 2008/0066272 A1 | 3/2008 | Hammerslag et al. |
| 2008/0066345 A1 | 3/2008 | Hammerslag et al. |
| 2008/0066346 A1 | 3/2008 | Hammerslag et al. |
| 2008/0083135 A1 | 4/2008 | Hammerslag et al. |

(56) References Cited

U.S. PATENT DOCUMENTS

| | | |
|---|---|---|
| 2008/0091132 A1 | 4/2008 | Bonutti |
| 2008/0249448 A1 | 10/2008 | Stevenson et al. |
| 2008/0294079 A1 | 11/2008 | Sterling et al. |
| 2008/0319362 A1 | 12/2008 | Joseph |
| 2009/0030353 A1 | 1/2009 | Bonutti et al. |
| 2009/0054819 A1 | 2/2009 | Einarsson |
| 2009/0090026 A1 | 4/2009 | Mosher |
| 2009/0099495 A1 | 4/2009 | Campos et al. |
| 2009/0099562 A1 | 4/2009 | Ingimundarson et al. |
| 2009/0105622 A1 | 4/2009 | Sterling et al. |
| 2009/0124948 A1 | 5/2009 | Ingimundarson et al. |
| 2009/0240181 A1 | 9/2009 | Sreeramagiri et al. |
| 2009/0259154 A1 | 10/2009 | Nace |
| 2009/0287128 A1 | 11/2009 | Ingimundarson et al. |
| 2010/0010409 A1 | 1/2010 | Bejarano |
| 2010/0056970 A1 | 3/2010 | Nace |
| 2010/0139057 A1 | 6/2010 | Soderberg et al. |
| 2010/0162539 A1 | 7/2010 | Rancon |
| 2010/0268139 A1 | 10/2010 | Garth |
| 2010/0274364 A1 | 10/2010 | Pacanowsky et al. |
| 2010/0299959 A1 | 12/2010 | Hammerslag et al. |
| 2011/0046528 A1 | 2/2011 | Stevenson et al. |
| 2011/0082402 A1 | 4/2011 | Oddou et al. |
| 2011/0098618 A1 | 4/2011 | Fleming |
| 2011/0144554 A1 | 6/2011 | Weaver, II et al. |
| 2011/0178448 A1 | 7/2011 | Einarsson |
| 2011/0184326 A1 | 7/2011 | Ingimundarson et al. |
| 2011/0197362 A1 | 8/2011 | Chella et al. |
| 2011/0266384 A1 | 11/2011 | Goodman et al. |
| 2012/0010547 A1 | 1/2012 | Hinds |
| 2012/0029404 A1 | 2/2012 | Weaver, II et al. |
| 2012/0046585 A1 | 2/2012 | Lee et al. |
| 2012/0059296 A1 | 3/2012 | Kompa |
| 2012/0157902 A1 | 6/2012 | Castillo et al. |
| 2013/0110020 A1 | 5/2013 | Ingimundarson et al. |
| 2013/0172797 A1 | 7/2013 | Merkley et al. |
| 2013/0178771 A1 | 7/2013 | Moir et al. |
| 2013/0331754 A1 | 12/2013 | Dunn et al. |
| 2014/0123449 A1 | 5/2014 | Soderberg et al. |

FOREIGN PATENT DOCUMENTS

| | | |
|---|---|---|
| CH | 577 282 A5 | 7/1976 |
| CH | 612 076 A5 | 7/1979 |
| CH | 624 001 A5 | 7/1981 |
| DE | 2 341 658 A1 | 3/1974 |
| DE | 33 20 274 A1 | 12/1984 |
| DE | 38 22 113 A1 | 1/1990 |
| DE | 93 15 776 U1 | 2/1995 |
| DE | 295 03 552 U1 | 4/1995 |
| DE | 196 31 632 A1 | 2/1998 |
| DE | 196 45 076 A1 | 5/1998 |
| DE | 198 11 925 A1 | 10/1999 |
| DE | 199 45 045 A1 | 3/2001 |
| DE | 100 57 286 A1 | 5/2002 |
| DE | 10 259 751 A1 | 7/2004 |
| DE | 10 2010 006 089 A1 | 8/2010 |
| EP | 0 201 051 A1 | 11/1986 |
| EP | 0 393 380 B1 | 9/1992 |
| EP | 0 589 233 A1 | 3/1994 |
| EP | 0 614 624 A1 | 9/1994 |
| EP | 0 614 625 A1 | 9/1994 |
| EP | 0 589 232 B1 | 11/1995 |
| EP | 0 841 044 A1 | 5/1998 |
| EP | 0 693 260 B1 | 9/1998 |
| EP | 0 651 954 B1 | 2/1999 |
| EP | 0 941 722 A1 | 9/1999 |
| EP | 1 114 619 A1 | 7/2001 |
| EP | 1 236 412 A1 | 9/2002 |
| EP | 1 302 184 A1 | 4/2003 |
| EP | 1 575 464 A1 | 9/2005 |
| EP | 1 880 802 A2 | 1/2008 |
| EP | 2 612 624 A1 | 7/2013 |
| FR | 2 122 846 A5 | 9/1972 |
| FR | 2 177 294 A6 | 11/1973 |
| FR | 2 399 811 A1 | 3/1979 |
| FR | 2 486 852 A1 | 1/1982 |
| FR | 2 663 380 A1 | 12/1991 |
| FR | 2 723 842 A1 | 3/1996 |
| FR | 2 777 489 A1 | 10/1999 |
| FR | 2 828 093 A1 | 2/2003 |
| GB | 1 213 855 A | 11/1970 |
| GB | 2 433 204 A | 6/2007 |
| JP | 3031760 U | 12/1996 |
| JP | 2004-016732 A | 1/2004 |
| JP | 2004-041666 A | 2/2004 |
| WO | 86/04228 A1 | 7/1986 |
| WO | 95/03720 A2 | 2/1995 |
| WO | 95/27451 A1 | 10/1995 |
| WO | 96/16615 A1 | 6/1996 |
| WO | 97/03581 A1 | 2/1997 |
| WO | 00/53045 A1 | 9/2000 |
| WO | 2004/056293 A1 | 7/2004 |
| WO | 2004/110197 A2 | 12/2004 |
| WO | 2006/044423 A2 | 4/2006 |
| WO | 2007/016983 A1 | 2/2007 |
| WO | 2010/087899 A2 | 8/2010 |

OTHER PUBLICATIONS

"Rollerblade TFS Skate Laces MICRO", http://www.inlinewarehouse.com/viewlarge.html?PCODE=MILC, retrieved on Jan. 7, 2010, 1 page.

Defrate, Louis E., et al., "In Vivo Function of the Posterior Cruciate Ligament During Weightbearing Knee Flexion", The American Journal of Sports Medicine, Dec. 2004, pp. 1923-1928, vol. 32, No. 8, Publisher: American Orthopaedic Society for Sports Medicine, Published by SAGE; http://ajs.sagepub.com/content/32/8/1923.

Cascade, "Jack PCL Brace", Oct. 2004, Publisher: Cascade Orthopedic Supply, Inc., Published in: US. http://www.cascade-usa.com/customer/caorsu/images/PDF/SSN_jackPCL.pdf.downloaded, 1 page.

Markolf, Keith L., et al., "Changes in Knee Laxity and Ligament Force After Sectioning the Posteromedial Bundle of the Posterior Cruciate Ligament", Arthroscopy: The Journal of Arthroscopic and Related Surgery, Oct. 2006, pp. 1100-1106, vol. 22, No. 10, Publisher: Arthroscopy Association of North America, Published in: US.

Papannagari, Ramprasand, et al., "Function of Posterior Cruciate Ligament Bundles During In Vivo Knee Flexion", The American Journal of Sports Medicine, Sep. 2007, pp. 1507-1512, vol. 35, No. 9, Publisher: American Orthopaedic Society for Sports Medicine, Published by SAGE; http://ajs.sage.pub.com/content/35/9/1507.

Bledsoe Axiom/Axiom-D Custom & OTS Knee Brace, "Application Instructions & Patient Manual: Instructions for ACL or PCL Symptoms", Jan. 2007, pp. 1-4, vol. CP020223, Rev B, Publisher: Bledsoe Brace Systems, Published in: US. http://www.bledsoebrace.com/pdf/AI/Axiom-AI.pdf.

Brochure: Armor Fourcepoint, Donjoy Product pages http://www.donjoy.com/armorfp. Downloaded, Oct. 2011, 2 pages. Published: US.

Brochure: "Fusion OA", BREG 360 Customer Care, Product page http://www.breg.com/knee-bracing/oa/fusion-oa.html, downloaded, Oct. 2011, 2 pages. Publisher: Orthofix, Published in: US.

Brochure: "Fusion XT OA", BREGG 360 Customer Care, Product page http://www.breg.com/knee-bracing/oa/fusion-xt-oa.html, downloaded, Oct. 2011, 2 pages. Publisher: Orthofix, Published in: US.

Brochure: "CTI Custom", OSSUR Product page from http://www.ossur.com/?PageID=13230 downloaded, Oct. 2011, 2 pages. Publisher: Ossur Americas, Published in: US.

Brochure: "X2K-OA", BREGG 360 Customer Care, Product page http://www.breg.com/knee-bracing/oa/x2k-oa.html. Downloaded, Oct. 2011, 1 page. Publisher: Orthofix, Published in: US.

International Search Report and Written Opinion regarding Application No. PCT/US2011/051627, dated Jan. 6, 2012.

International Search Report from corresponding PCT Application No. PCT/US2012/062702, dated Feb. 15, 2013.

International Preliminary Report on Patentability regarding Application No. PCT/US2011/051627, dated Mar. 28, 2013.

(56) References Cited

OTHER PUBLICATIONS

Menetrey, Jacques, "PCL: Conservative Treatment", 4th Advanced Course on Knee Surgery, Jan. 22-27, 2012. http://www.kneecourse.com/download/seminar_2012/monday/MENETREY%20Conservative%20treatment.pdf, 37 pages.

Extended European Search Report from EP Application No. 12150517.6, dated May 22, 2012.

Smith, Sean D. et al., "Functional bracing of ACL injuries: current state and future directions", Knee Surgery Sports Traumatology Arthhroscopy, Springer, Apr. 27, 2013, 11 pages.

Knapik, Joseph J. et al., Isometric, Isotonic and Isokinetic Torque Variations in Four Muscle Groups Through a Range of Joint Motion, "Physical Therapy: Journal of the American Physical Therapy Association and de Fysiotherapeut", 1983, vol. 63, No. 6, pp. 938-947, downloaded from http://ptjournal.apta.org/ on Apr. 15, 2014.

International Search Report and Written Opinion from International Application No. PCT/US2014/013245, dated May 6, 2014.

Jansson, Kyle S. et al., "A Historical Perspective of PCL Bracing", Knee Surgery Sports Traumatology Arthhroscopy, Springer-Verlag, May 24, 2012, 7 pages.

International Search Report from corresponding International Application No. PCT/US2014/042989, dated Oct. 15, 2014.

International Search Report from International Application No. PCT/US2009/004714, dated Dec. 2, 2009.

International Search Report from corresponding International PCT Application No. PCT/US2015/039672, dated Oct. 1, 2015.

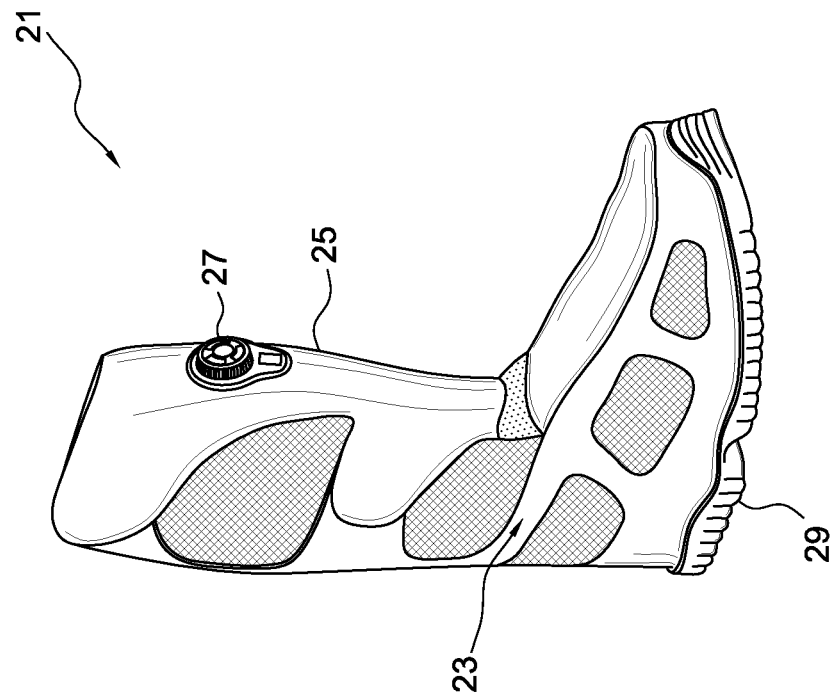
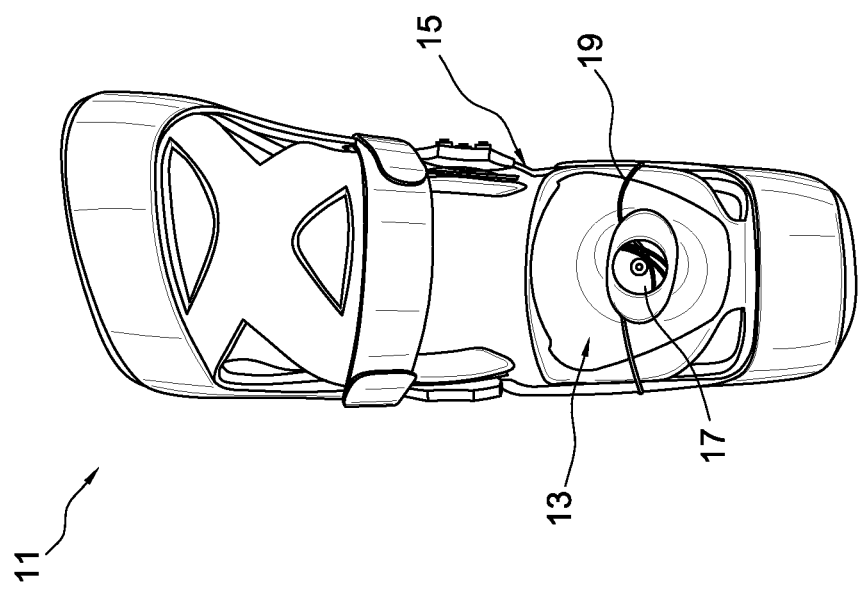

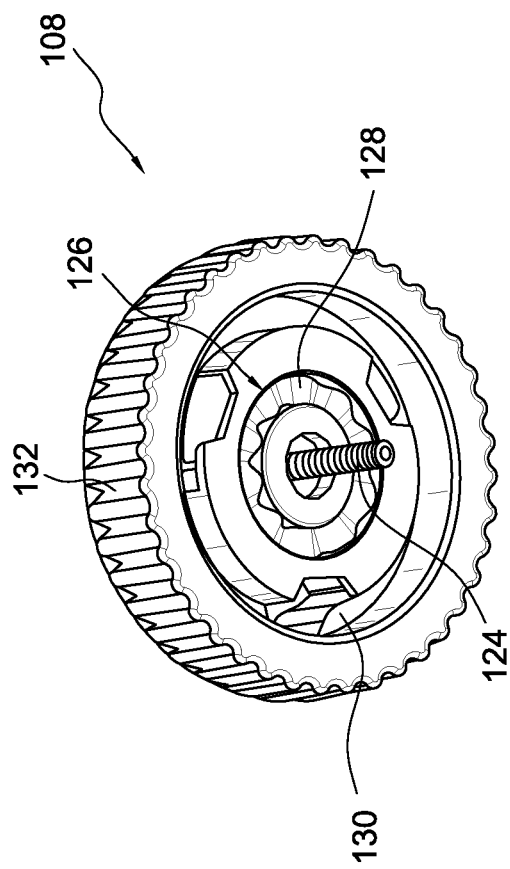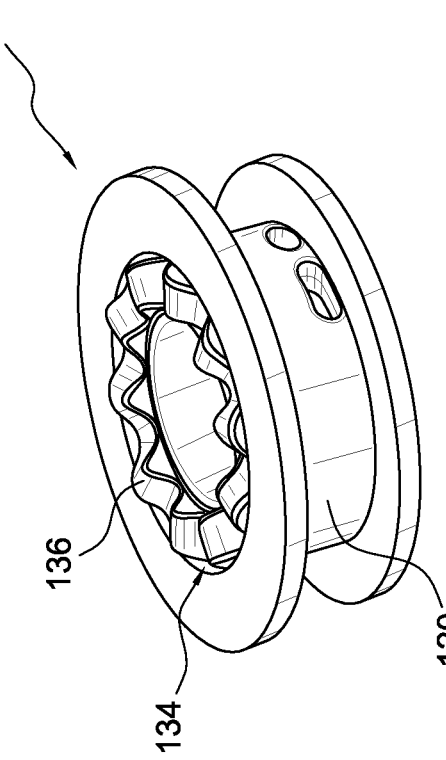

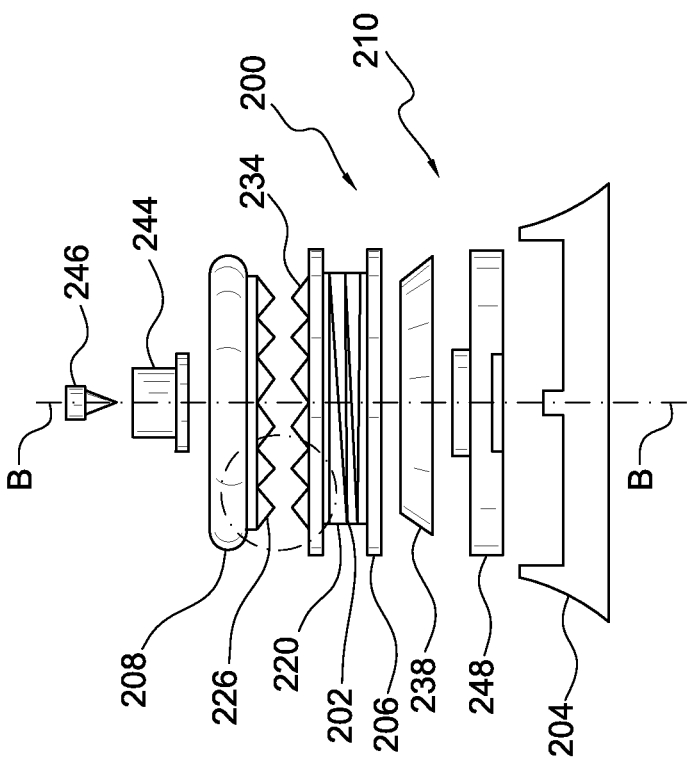
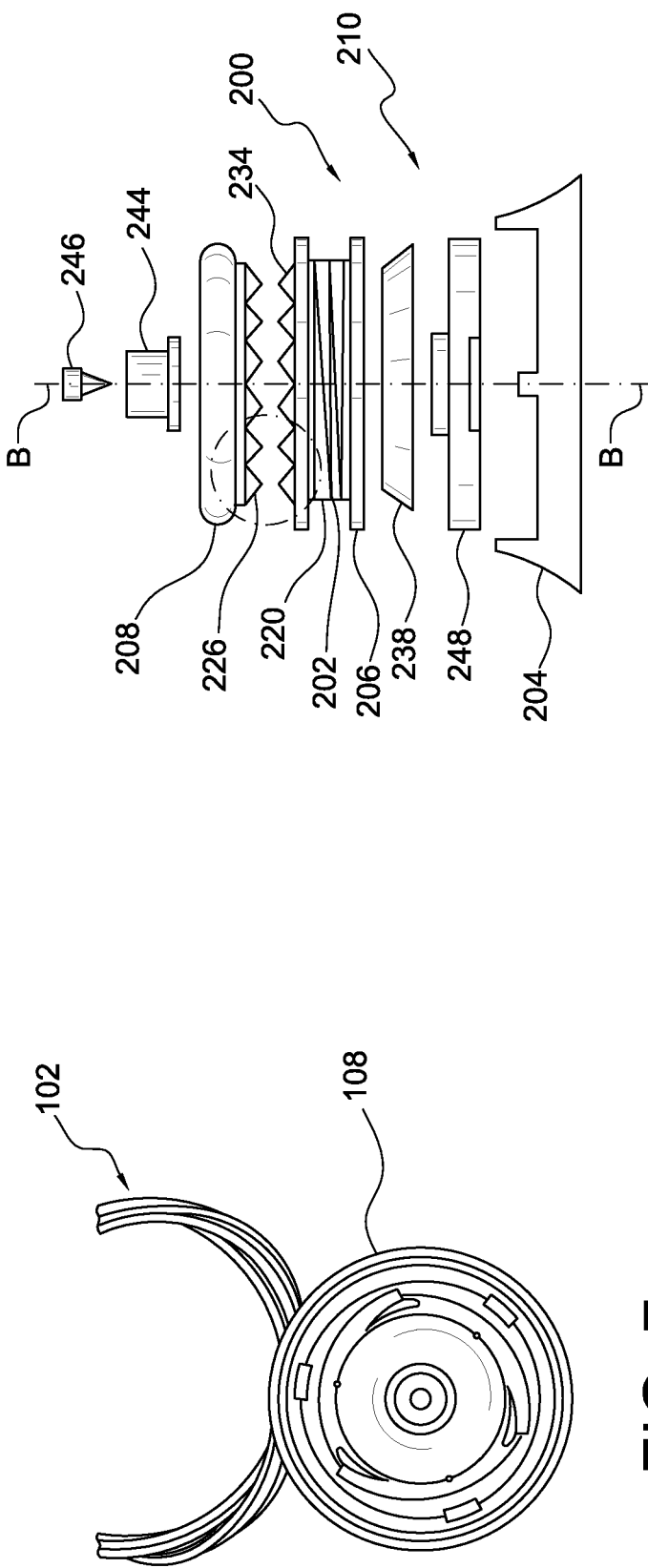
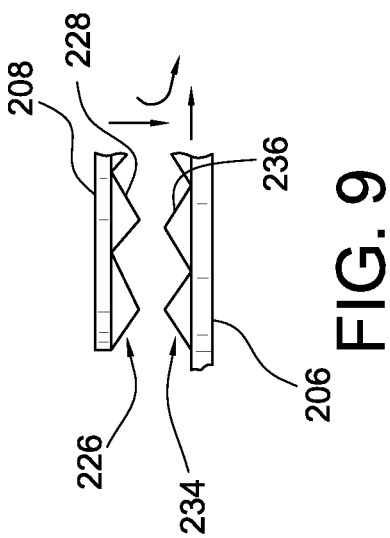

TIGHTENING SYSTEM WITH A TENSION CONTROL MECHANISM

TECHNICAL FIELD

The disclosure relates to a tightening system with a tension control mechanism.

BACKGROUND

There are a variety tightening or closure systems that employ a lace or cable based reel for tightening an article, such as orthopedic or prosthetic devices. One conventional type of tightening system includes a lace attached to a rotary tightening system which allows for incremental adjustment of the tension of the lace.

While such tightening systems can be effective at tightening an article over a user, they suffer from a number of drawbacks. One of these drawbacks is the inability to prevent over tensioning of the system. As a result, there is a risk that the user may over tighten the system, and cause injury to the user. For instance, in an orthopedic device which requires precise and prescribed tightening to treat an injury, the user must not further aggravate the injury by creating too much pressure over the injury due to excessive tightening of the tightening system. Further, known tightening systems lack the ability to adjust the maximum tension limit of the lace, significantly hindering the functionality of the tightening system in various treatment protocols.

It can be seen from the foregoing there are many needs for improving on the drawbacks of conventional tightening systems. The embodiments of the present disclosure address these aforementioned shortcomings.

SUMMARY

Embodiments of the tightening system provide the ability to automatically release tension in the tightening system when such tension reaches a predetermined level. By automatically limiting or regulating the level of tension in the tightening system, the tightening system can reduce the likelihood that a user will over-tighten the system about an anatomical member of the user. This is advantageous because over-tightening can cause pressure on the skin, which can reduce both capillary blood flow to the skin and arterial flow to the anatomical member. Over-tightening can also cause undesirable and/or excessive loads on the user's bones and/or joints. It should be appreciated that the tightening system can prevent over tensioning of the system during initial tensioning and/or in use.

It is a goal of the present disclosure to reduce the need of users themselves having to set or monitor safe tension levels within the tightening system. For instance, conventional tightening systems often require users to monitor tension in the tightening system based on how tight the orthopedic or prosthetic device feels on the user's limb. However, many users, especially users with an injured or affected limb, experience irregular sensation. Consequently, such users are at risk of over-tightening or under tightening the tightening system, causing injury to the user. By including a tension control mechanism in the tightening system that automatically releases excess tension, the user can tighten the tightening system without the need of monitoring safe or target tension levels.

It is another goal of the present disclosure to offer the ability to adjust the maximum tension limit of the tightening system. The tightening system of various embodiments offer a practical solution for a user to adjust the maximum tension limit on the fly during use or when initially donning an article including the tensioning system. This advantageously increases the operational functionality of the tightening system in various treatment protocols.

In an embodiment, a tightening system includes a housing and a spool situated within the housing. The spool is rotatable about an axis within the housing. An elongate tensioning element is rotatably linked to the spool and a tension control mechanism is operatively connected to the spool. The tension control mechanism is arranged to automatically move relative to the spool when tension in the tensioning element reaches a predetermined level, which, in turn, releases at least some of the tension in the tensioning element.

In some embodiments, the tightening system includes a sensitivity adjustment dial arranged to selectively adjust an actuating or maximum tension of the tension control mechanism. Thus, a user, clinician, or medical professional can advantageously adjust the actuating tension of the tension control mechanism to customize the tightening system for different users and/or user needs. For instance, a clinician can adjust the actuating tension during the course of treatment where the maximum load may vary.

Additional features and advantages of embodiments of the present disclosure will be set forth in the description that follows, and in part will be obvious from the description, or may be learned by the practice of such exemplary embodiments. These and other features will become more fully apparent from the following description and appended claims, or may be learned by the practice of such exemplary embodiments as set forth.

BRIEF DESCRIPTION OF THE DRAWINGS

To further clarify the above and other advantages and features of the present disclosure, a more particular description of the disclosure will be rendered by reference to specific embodiments illustrated in the drawings. It is appreciated that these drawings depict only typical embodiments of the disclosure and are not to be considered limiting of scope, and are not necessarily drawn to scale. The disclosure will be described and explained with additional specificity and detail through the use of the accompanying drawings.

FIG. 1 is an isometric view of a knee brace in which the exemplary embodiments of a tightening system may be implemented.

FIG. 2 is an isometric view of circumferential type walking boot (walker) in which the exemplary embodiments of a tightening system may be implemented.

FIG. 5 is an isometric view of a dial according to an embodiment.

FIG. 6 is an isometric view of a spool according to an embodiment.

FIG. 7 is an isometric view of a dial and tensioning element according to an embodiment.

FIG. 8 is an exploded view of a tightening system according to another embodiment.

FIG. 9 is a partial detailed view of the dial and the spool shown in FIG. 8.

DETAILED DESCRIPTION

Figure 4:
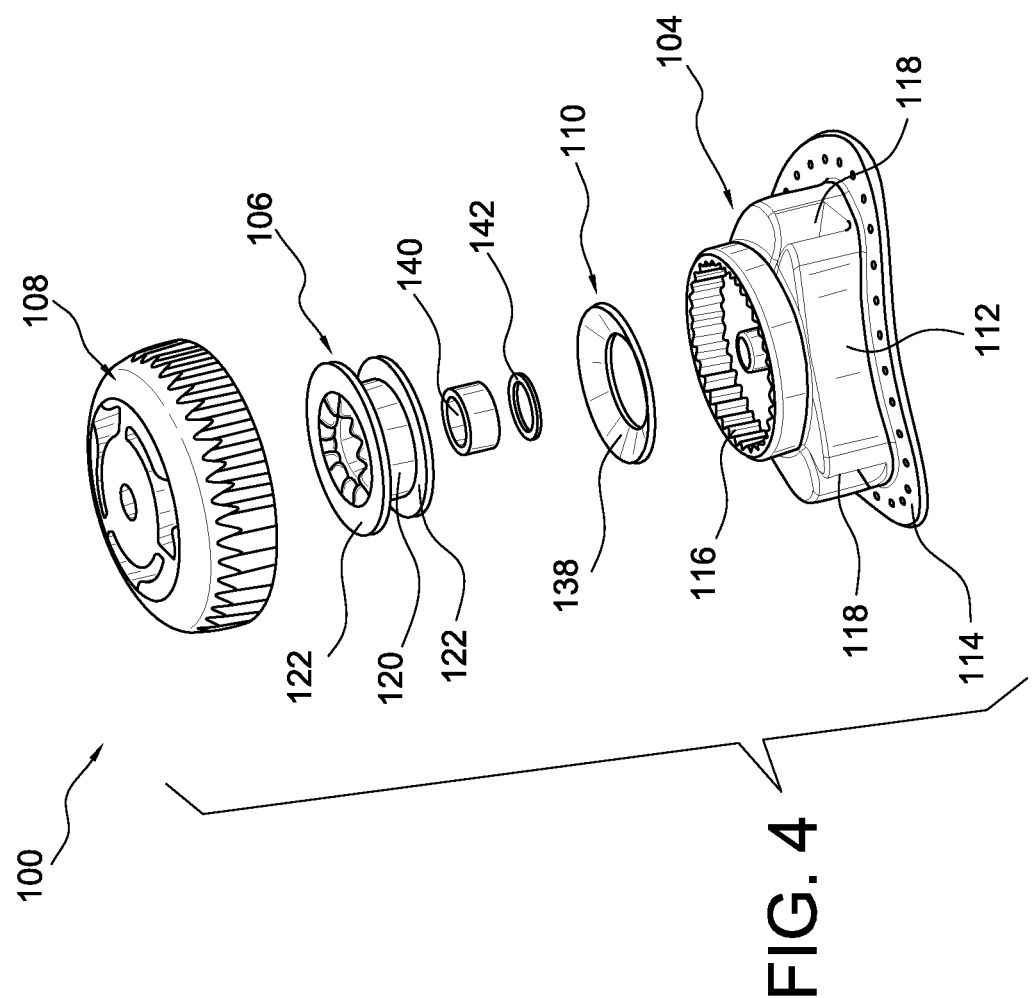
FIG. 4 is an exploded view of the tightening system shown in FIG. 3.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

For further ease of understanding the exemplary embodiments as disclosed herein, a description of a few terms is necessary. As used herein, the term "dorsal" has its ordinary meaning and refers to the top surfaces of the foot, ankle and foreleg or shin. As used herein, the term "plantar" has its ordinary meaning and refers to a bottom surface, such as the bottom of a foot. As used herein, the term "proximal" has its ordinary meaning and refers to a location that is closer to the heart than another location. Likewise, the term "distal" has its ordinary meaning and refers to a location that is further from the heart than another location. The term "posterior" also has its ordinary meaning and refers to a location that is behind or to the rear of another location. Lastly, the term "anterior" has its ordinary meaning and refers to a location that is ahead of or to the front of another location.

The terms "rigid," "flexible," and "resilient" may be used herein to distinguish characteristics of portions of certain features of the orthopedic device. The term "rigid" is intended to denote that an element of the device is generally devoid of flexibility. Within the context of support members or shells that are "rigid," it is intended to indicate that they do not lose their overall shape when force is applied, and in fact they may break if bent with sufficient force.

On the other hand, the term "flexible" is intended to denote that features are capable of repeated bending such that the features may be bent into retained shapes or the features do not retain a general shape, but continuously deform when force is applied. The term "resilient" is used to qualify such flexible features as generally returning to an initial general shape without permanent deformation. As for the term "semi-rigid," this term is used to denote properties of members that provide support and are free-standing; however such members may have some degree of flexibility or resiliency.

The exemplary embodiments of a tightening system can be used in various articles, including, but not limited to, configurations of knee braces, wrist braces, ankle braces, cervical collars, elbow braces, walking boots, orthopedic shoes, post-surgical shoes, prosthetic devices, footwear, athletic gear, prosthetic sockets, traction devices, or any other suitable article.

For example, exemplary embodiments of a tightening system can be implemented with a knee brace 11, as shown in FIG. 1. An exemplary knee brace 11 includes a shell 13 connected to a frame 15. In this exemplary device 11, a tightening system 17 is secured on the shell 13. The tightening system 17 can be arranged to draw the shell 13 toward a limb of a user by tensioning an elongate tensioning element 19, such as a cable or lace, wound by the tightening system 17 and connected to the frame 15. It will be appreciated that the tightening system 17 can be secured to the frame, a strap, or any other suitable component of the knee brace 11.

Further, exemplary embodiments of a tightening system can be implemented with a walker 21, as shown in FIG. 2. The walker 21 can include a base shell 23 and a dorsal shell 25, such that the lower leg is generally fully enclosed and supported by the walker 21. An outsole 29 can be provided along the distal planar surface of the walker 21. The dorsal shell 25 can be moveable away from and towards the base shell 23 in order to open and close the walker 21. A tightening system 27 can be secured to the walker 21 that utilizes an elongate tensioning element, such as a cable or lace, to simultaneously and incrementally tighten the components of the walker 21 around the lower leg.

Figure 3:
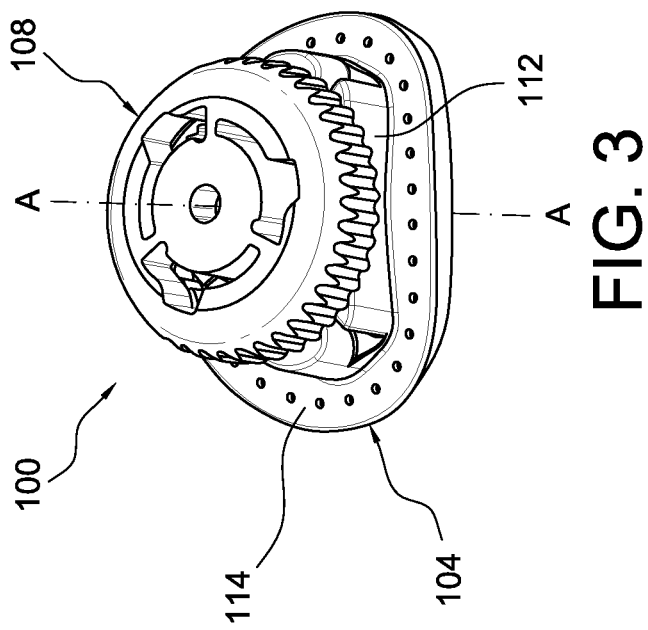
FIG. 3 is an isometric view of a tightening system according to an embodiment.

Referring now to FIGS. 3-7, a first exemplary embodiment of a tightening system comprises a tightening system 100 including at least one tensioning element 102 (shown in FIG. 7), a base 104, a spool 106 (shown in FIG. 4), and a dial 108. The spool 106 can be situated within the base 104 such that the spool 106 (shown in FIG. 4) is rotatable about an axis A-A (shown in FIG. 3) relative to the base 104. The tensioning element 102 can be rotatably linked to the spool 106. The tensioning element 102 (best seen in FIG. 7) may be formed from any type of line, cord, strap, rope, string, wire, cable or other suitable element. Further, the tightening system 100 may include one, two, three, four, or any other suitable number of tensioning elements.

When the spool 106 rotates in a tightening direction, the tensioning element 102 is drawn into the base 104 and is wound around the spool 106. As the tensioning element 102 is wound around the spool 106, tension in the tensioning element 102 increases, causing the system 100 to tighten. When the spool 106 rotates in a loosening direction, the tensioning element 102 unwinds from the spool 106 and at least a part of the tensioning element 102 exits the base 104. As the tensioning element 102 (shown in FIG. 7) unwinds from the spool 106, tension in the tensioning element 102 decreases, loosening the system 100. The spool 106 can include a first engagement surface 126 (shown in FIG. 5) described in more detail below.

The dial 108 can be attached to the base 104 such that the dial 108 can rotate about the axis A-A relative to the base 104. The dial 108 can include a second engagement surface 134 (shown in FIG. 6) arranged to mate with the first engagement surface 126 of the spool 106. This arrangement can couple the dial 108 to the spool 106 so that the tension in the tensioning element 102 can be manually controlled by twisting the dial 108. For instance, rotation of the dial 108 in the tightening direction can cause the spool 106 to rotate in the tightening direction, increasing tension in the tensioning element 102. Rotation of the dial 108 in the loosening direction can cause the spool 106 to rotate in the loosening direction, decreasing tension in the tensioning element 102.

The system 100 includes a tension control mechanism 110 configured to automatically release tension in the tensioning element 102 when the tension in the tensioning element 102 reaches a predetermined level. For instance, the tension control mechanism 110 can enable the engagement surfaces of the spool 106 and the dial 108 to be engaged or disengaged in response to the presence of a predetermined level of tension (e.g., a maximum tension level) in the tensioning element 102. When tension in the tensioning element 102 reaches the predetermined level, the tension control mechanism 110 can be actuated to automatically disengage the first engagement surface 126 of the spool 106 from the second engagement surface 134 of the dial 108. This allows the spool 106 to spin in the loosening direction, which, in turn, releases excess or at least part of the tension in the tensioning element 102. When the tension in the tensioning element 102 drops back below the predetermined level, the tension control mechanism 110 can function to automatically reengage the engagement surfaces 126, 134 of the spool 106 and the dial 108.

Because the tension control mechanism 110 can automatically limit or regulate the level of tension in the tensioning element 102, the tension control mechanism 110 advantageously can reduce the likelihood that a user will over-tighten the tightening system 100 as found in the prior art. This is important because over-tightening can cause pressure on the skin, which can reduce both capillary blood flow to the skin and arterial flow to the anatomical member. Over-tightening can also cause undesirable and/or excessive loads on the user's bones and/or joints. Thus, by limiting or automatically regulating the level of tension in the tensioning element 102, the tension control mechanism 110 eliminates or reduces the likelihood of over-tightening that can harm the user. It will be appreciated that the tension control mechanism 110 can prevent over tensioning of the system 100 during initial tensioning and in use.

The tension control mechanism 110 can reduce the need for users themselves to set or monitor safe tension levels within the tightening system 100. For instance, conventional tightening systems often require users to monitor tension in the tightening system based on how tight the orthopedic device feels on the user's limb. However, many users, especially users with an injured limb, experience irregular sensation in the user's injured limb. Consequently, such users are at risk of over-tightening or under tightening the tightening system 100, causing injury to the user. By including the tension control mechanism 110 in the tightening system 100, the user can tighten the tightening system 100 without the need of monitoring safe or target tension levels. It should be appreciated that many variations of the tension control mechanism 110 having different shapes and sizes can be used for automatically limiting or regulating the tension level in the tensioning element 102. Although such variations may differ in form, they perform substantially similar functions.

The construction of the tightening system 100 will now be discussed in greater detail in connection with FIGS. 4-7. As noted above, the tightening system 100 can include the base 104, the spool 106, and the dial 108. The base 104 can include a housing 112 and a mounting flange 114. The housing 112 can include a plurality of housing teeth 116, which can extend radially inwardly. The housing 112 can also include one or more tension element holes 118 adapted for allowing the tensioning element 102 to enter and/or exit the housing 112. It should be appreciated that many variations of the base 104 having different shapes and/or sizes can be used. The housing 112 and the mounting flange 114 can comprise a single member or a plurality of members coupled together.

The spool 106 can be situated within the housing 112 such that the spool 106 is rotatable about the axis A-A relative to the housing 112. The spool 106 can define a cylindrical winding surface 120 extending circumferentially between a pair of annular flanges 122. The tensioning element 102 can be rotatably linked to the spool 106 such that when the spool 106 is rotated in the tightening direction, the tensioning element 102 is drawn into the housing 112 and is wound around the winding surface 120. When the spool 106 rotates in the loosening direction the tensioning element 102 unwinds from the winding surface 120 and exits the housing 112 via the tension element holes 118. While the winding surface 120 is describes as being cylindrical, the winding surface 120 can be elliptical, triangular, or may have any other suitable shape.

As best seen in FIGS. 5 and 6, the dial 108 can be attached to the housing 112 via a fastener 124 such that the dial 108 can rotate about the axis A-A with respect to the housing 112. The dial 108 includes a first engagement surface 126 comprising a wavy profile with a first plurality of waves 128. The first engagement surface 126 can be located on the lower surface of the dial 108.

Optionally, the dial 108 can also include one or more pawls 130 which can be biased radially outward so as to mate with the housing teeth 116. The pawls 130 and the housing teeth 116 can be configured so that the housing teeth 116 can displace the pawls 130 radially inwardly when the dial 108 is rotated in the tightening and/or loosening directions, thereby allowing the dial 108 to incrementally rotate in the tightening and loosening directions. The radially outer surface of the dial 108 can include a grip portion 132 configured to help a user grip the dial 108 while manipulating the dial 108.

The spool 106 can define a second engagement surface 134 mutually opposed the first engagement surface 126. The second engagement surface 134 can be located on the upper surface of the spool 106 and can form a wavy profile with a second plurality of waves 136. The second waves 136 of the second engagement surface 134 are configured to mate with the first waves 128 of the first engagement surface 126 to couple the dial 108 to the spool 106 such that rotation of the dial 108 in the tightening direction causes the spool 106 to also rotate in the tightening direction. Rotation of the dial 108 in the loosening direction can also cause the spool 106 to rotate in the loosening direction.

Thus, the dial 108 can be rotated in the tightening direction, causing the spool 106 to rotate in the tightening direction, which, in turn, causes the tensioning element 102 to be drawn into the housing 112. As the tensioning element 102 is drawn into the housing 112, the tension level in the tensioning element 102 increases and the system 100 tightens. The dial 108 can be rotated in the loosening direction, causing the spool 106 to rotate in the loosening direction, which, in turn, causes the tension level in the tensioning element 102 to decrease. The waves of the first and second engagement surfaces can be configured such that any torque transfer between the dial 108 and the spool 106 creates a downward displacement force or in other words pushes the spool 106 away from the dial 108.

Referring again to FIG. 4, the tightening system 100 can include a bushing 140 and/or washer 142 in between components to help properly align, space, and/or fasten the individual components of the tightening system 100. The bushing 140 and/or washer 142 can also help reduce friction between moving parts in the tightening system 100.

In the illustrated embodiment, the tension control mechanism 110 can comprise a resilient member 138 situated under the spool 106. The resilient member 138 can comprise a conical spring or a Belleville washer. As seen, the resilient member 138 can be arranged such that a diameter of the resilient member 138 tapers toward the base 102.

The resilient member 138 can move between an original position and a release position. In the original position, the resilient member 138 can have a shape with at least a part of the upper surface of the resilient member 138 engaging the lower surface of the spool 106. This arrangement can exert an opposing force on the spool 106 that counters the downward displacement force on the spool 106 when torque is transferred between the dial 108 and the spool 106. It will be appreciated that the resilient member 138 can have a generally convex shape, a generally concave shape, a u-shape, or any other suitable shape. In other embodiments, the resilient member 138 can comprise a wave washer or wave spring formed in an irregular shape. A variety of suitable materials, including different metals, elastomeric materials, plastics, rubbers, and/or resins, may produce the resilient member 138.

The opposing force from the resilient member 138 can bias the spool 106 toward the dial 108 to maintain the first engagement surface 126 of the dial 108 engaged with the second engagement surface 134 of the spool 106. The resilient member 138 can use at least in part its material properties (e.g., elasticity) and its preloaded shape to generate the opposing force against the spool 108. In the release position, the resilient member 138 is compressed or has a more flattened shape so that the spool 106 can move axially away from the dial 108, allowing the engagement surfaces to disengage.

As noted above, the downward displacement force can be generated by torque transfer between the dial 108 and the spool 106. The torque transfer can result from twisting of the dial 108 and/or spool 106 and/or tension in the tensioning element 102. The level of tension in the tensioning element 102 can thus correspond to the magnitude of the downward displacement force. For instance, a greater level of tension in the tensioning element 102 can cause a greater downward displacement force on the spool 106.

When the downward displacement force on the spool 106 exceeds the opposing force of the resilient member 138 on the spool 106, the downward displacement force can cause the resilient member 138 to automatically move or flex from the original position to the release position. In the release position, the second engagement surface 134 of the spool 106 can disengage from the first engagement surface 126 of the dial 108. This can allow the spool 106 to spin in the loosening direction, which, in turn, releases excess or at least part of the tension in the tensioning element 102. When the downward displacement force exerted on the spool 106 is less than the opposing force from the resilient member 138, the resilient member 138 can naturally and/or automatically return to the original position such that the engagement surfaces reengage.

The point at which the tension level of the tensioning element triggers or moves the resilient member 138 to the release position is called the actuating tension. It will be appreciated that the actuating tension can be selected or set in any suitable manner. For instance, the actuating tension can be selected or set by utilizing a resilient member 138 having specific material properties and/or a specific preloaded shape. The actuating tension can be selected or set by utilizing a plurality of resilient members 138. The actuating tension can be set by selectively preloading of the resilient member 138.

In an embodiment, the actuating tension can be adjustable. For instance, the actuating tension can be adjusted by customizing the system 100 with one or more resilient members 138 having specific characteristics and/or adjusting the preload on the resilient member 138. Thus, a user, clinician, or medical professional can advantageously adjust the actuating tension to customize the tightening system 100 for different users and/or user needs. In other embodiments, the actuating tension can be selected or set by a clinician or medical professional to correspond to a safe or proper tightness of the tightening system 100.

As previously discussed, the actuating tension can be selected or set to automatically limit or regulate a maximum tension level in the tensioning element 102. This advantageously reduces the likelihood that a user will over-tighten the tightening system 100. This is important because over-tightening can cause pressure on the skin, which can reduce both capillary blood flow to the skin and arterial flow to the anatomical member. Over-tightening can also cause undesirable and/or excessive loads on the user's anatomical limb. Thus, by limiting or automatically regulating the level of tension in the tensioning element 102, the tension control mechanism 110 eliminates or reduces the likelihood of over-tightening that can harm the user. The tension control mechanism 110 also can reduce the need for users themselves to set or monitor safe tension levels within the tightening system 100.

It will be appreciated that the resilient member 138 is exemplary only, as other tension control mechanisms are possible. For instance, the tension control mechanism can comprise at least one coil spring, a torsion spring, a Belleville washer, one or more spring bars, a resiliently compressible member, combinations thereof, or any other suitable member. In other embodiments, the first and second engagement surfaces may include any number of different profiles that permit engagement and disengagement of the first and second engagement surfaces. For instance, the profile may be sinusoidal or serrated. While both engagement surfaces are shown including general the same profile, in other embodiments, the first engagement surface can have a profile that is different from the profile of the second engagement surface. While the engagement surfaces are shown located on the bottom surface of the dial 108 and the upper surface of the spool 106, the engagement surfaces may be located in any suitable location. For example, the first engagement surface may be located on an inner radial surface of the dial 108 and the second engagement surface may be located on an outer radial surface of the spool 106.

FIGS. 8 and 9 illustrate an embodiment of a tightening system 200 having a sensitivity adjustment dial 244 capable of adjusting the actuating tension of the tension control mechanism 210 of the system 200. As shown, the adjustment dial 244 can be secured by a fastener 246 to a dial 208. The dial 208 defines a first engagement surface 226 formed as a serrated profile with a first plurality of teeth 228. The adjustment dial 244 can be connected to an upper surface of the dial 208, and the first engagement surface 226 can be located on a lower surface of the dial 208.

A spool 206 defines a generally cylindrical winding surface 220 for receiving at least a portion of the tensioning element 202. The spool 206 can include a second engagement surface 234 located at an upper surface of the spool 206 that is mutually opposed the first engagement surface 226. The second engagement surface 234 can form a serrated profile with a second plurality of teeth 236 configured for meshing or engaging the first plurality of teeth 228. It should be noted that the teeth of the first and second engagement surfaces are neither vertically nor counter-sloped relative to one another. From this arrangement, any torque transfer from the dial 208 to the spool 206 causes the downward displacement force on the spool 206.

Similar to the system 100, the first and second engagement surfaces are not limited to having a serrated profile, but may include any number of different profiles that permit engagement of the first and second engagement surfaces.

A tension control mechanism 210 can comprise the adjustment dial 244, a conical spring 238, and a sensitivity plate 248. The spring 238 can engage a lower surface of the spool 206. A lower surface of the spring 238 can engage the sensitivity plate 248. The spool 206 and sensitivity plate 248 can be rotatably connected to the base 204 along an axis B-B. As seen in FIG. 8, the spring 238 can be arranged such that a diameter of the spring 238 tapers toward the spool 206.

Like the resilient member 138, the spring 238 is movable between an original position, wherein the spring 238 exerts an opposing force on the spool 206 that maintains the engagement surfaces engaged, and a release position, wherein the downward displacement force on the spool 206 compresses the spring 238, causing the engagement surfaces to disengage. This allows the spool 206 to spin in the loosening direction, which, in turn, releases excess or at least part of the tension in the tensioning element 202.

The actuating tension required to compress the spring 238 sufficiently to move the spring 238 from the original position to the release position can depend in part on preloading of the spring 238. By turning the adjustment dial 244 in a specified direction, the sensitivity plate 248 moves either upwardly or downwardly (depending on the direction the adjustment dial 244 is turned) thereby causing more or less preload on the spring 238, and making the actuating tension more or less. Thus, a user, clinician, or medical professional can advantageously adjust the actuating tension to customize the tightening system 200 for different users and/or user needs. For instance, a clinician can adjust the actuating tension during the course of treatment where the maximum load may vary.

It will be appreciated that the embodiments of the tightening system are to be regarded as exemplary only. For instance, while one resilient member is shown, in other embodiments, the tightening system can include two, three, four, or any other suitable number of resilient members. It should also be appreciated that many variations of the tightening system having different shapes and/or sizes can be used. Although such variations may differ in form, they perform substantially similar functions.

The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

What is claimed is:

1. A tightening system comprising:
    a housing;
    a dial member connected to the housing;
    a spool situated within the housing, the spool defining a winding surface and selectively engaging the dial member such that rotation of the dial member causes rotation of the spool;
    an elongate tensioning element attached to the spool, the spool being rotatable in a first direction in which the elongate tensioning element is wound around the winding surface and a second direction in which the elongate tensioning element is unwound from the winding surface; and
    a tension control mechanism engaging a lower surface of the spool,
    wherein when a tension level in the tensioning element reaches a predetermined level the tightening system automatically moves from an original position in which the tension control mechanism forces the spool into engagement with the dial member to a release position in which the spool shifts away from the dial member and rotates independent of the dial member in the second direction to decrease the tension level in the elongate tensioning element.

2. The system of claim 1, wherein the tension control mechanism comprises at least one resilient member.

3. The system of claim 2, wherein the at least one resilient member comprises a conical spring.

4. The tightening system of claim 1, wherein the dial member defines a first engagement surface, and the spool defines a second engagement surface opposed the first engagement surface, the second engagement surface arranged to engage the first engagement surface such that rotation of the dial member causes rotation of the spool.

5. The tightening system of claim 4, wherein the first and second engagement surfaces are arranged so that torque transfer from the dial member causes a downward displacement force on the spool.

6. The tightening system of claim 4, wherein the tension control mechanism comprises a conical spring.

7. The system of claim 6, wherein the spool is arranged to freely spin when the second engagement surface disengages from the first engagement surface.

8. The tightening system of claim 4, wherein at least one of the first engagement surface and the second engagement surface defines a wavy profile.

9. The system of claim 1, wherein the predetermined tension level comprises a maximum tension level of the tensioning element.

10. The system of claim 1, wherein the predetermined tension level is variable by adjusting a relative position between the tension control mechanism and the housing.

11. The system of claim 1, wherein the tension control mechanism comprises a resilient member having a diameter that tapers toward a bottom portion of the housing.

12. An orthopedic system comprising:
    a tightening system including:
    a housing;
    a spool situated within the housing, the spool rotatable about an axis and defining a winding surface;
    a dial member selectively engaging the spool, wherein the dial member defines a first engagement surface, and the spool defines a second engagement surface opposed the first engagement surface, the second engagement surface arranged to engage the first engagement surface such that rotation of the dial member causes rotation of the spool;
    an elongate tensioning element rotatably linked to the spool, the spool being rotatable in a first direction in which the elongate tensioning element is wound around the winding surface and a tension level in the elongate tensioning element increases and a second direction in which the elongate tensioning element is unwound from the winding surface and the tension level in the elongate tensioning element decreases; and
    a resilient element situated under the spool, wherein when the tension level in the tensioning element reaches a predetermined level the at least one resilient member moves from an original position in which the least one resilient member forces the spool into engagement with the dial member to a release position in which the resilient element allows the second engagement surface to disengage from the first engagement surface and rotate independent of the dial member in the second direction to decrease the tension level in the elongate tensioning element.

13. The orthopedic system of claim 12, further comprising an orthopedic device including a frame connected to the tightening system.

14. The orthopedic system of claim 13, wherein the orthopedic device comprises a knee brace.

* * * * *